US012669560B2

(12) United States Patent
Dickmann et al.

(10) Patent No.: US 12,669,560 B2
(45) Date of Patent: Jun. 30, 2026

(54) HEAD-NECK COIL ARRANGEMENT FOR MAGNETIC RESONANCE APPLICATIONS

(71) Applicant: Siemens Healthineers AG, Forchheim (DE)

(72) Inventors: Christoph Dickmann, Nuremberg (DE); Martin Requardt, Nuremberg (DE); Hans Weber, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/980,408

(22) Filed: Dec. 13, 2024

(65) Prior Publication Data

US 2025/0195008 A1    Jun. 19, 2025

(30) Foreign Application Priority Data

Dec. 14, 2023    (DE) ..................... 10 2023 212 723.7

(51) Int. Cl.
    *G01R 33/34* (2006.01)
    *A61B 5/055* (2006.01)
    *G01R 33/36* (2006.01)

(52) U.S. Cl.
    CPC ........ *G01R 33/34084* (2013.01); *A61B 5/055* (2013.01); *G01R 33/36* (2013.01)

(58) Field of Classification Search
    CPC .............. A61B 5/055; G01R 33/34084; G01R 33/34046; G01R 33/34076; G01R 33/34092; G01R 33/341
    See application file for complete search history.

(56) References Cited

U.S. PATENT DOCUMENTS 4,891,596 A * 1/1990 Mitomi ................. A61B 5/704
                                                            324/318
8,099,150 B2    1/2012 Piferi et al.
                    (Continued)

FOREIGN PATENT DOCUMENTS

CN        215916247 U    3/2022
DE    102008063629 A1    7/2010
                    (Continued)

OTHER PUBLICATIONS

Konnert Dinah et al.; "Novel modified patient immobilisation device with an integrated coil support system for MR-guided online adaptive radiotherapy in the management of brain and head-and-neck tumours."; Technical Innovations & Patient Support in Radiation Oncology; 2021; 20. Jg; S. 35-40.

(Continued)

*Primary Examiner* — Carolyn A Pehlke

(74) *Attorney, Agent, or Firm* — Harness, Dickey & Pierce, P.L.C.

(57)    ABSTRACT

The coil arrangement comprises: a rigid base part with which the coil arrangement can be placed on a patient couch; an upper additional part including upper local coils, wherein the upper additional part is movable such that a spacing of the upper local coils from the facial, neck and upper chest area of the patient is adjustable; and a lower additional part including lower local coils. The base part, the lower additional part and the upper additional part are connected so as to be capable of being handled manually as one unit. The lower additional part, viewed from anterior to posterior, is adjustable in height relative to the base part to adjust a spacing of the lower local coils from the back of the head of the patient.

19 Claims, 2 Drawing Sheets

(56)                   References Cited

U.S. PATENT DOCUMENTS

| | | | | |
|---|---|---|---|---|
| 9,134,389 | B2 * | 9/2015 | Driemel ........... | G01R 33/34007 |
| 2004/0030241 | A1 * | 2/2004 | Green ................... | A61B 5/055 |
| | | | | 600/422 |
| 2010/0156420 | A1 | 6/2010 | Driemel | |
| 2012/0286784 | A1 | 11/2012 | Driemel | |
| 2018/0351296 | A1 * | 12/2018 | Driemel ................ | H01R 13/44 |
| 2021/0278489 | A1 * | 9/2021 | Iwasawa .......... | G01R 33/34084 |
| 2021/0369133 | A1 | 12/2021 | Coppens et al. | |

FOREIGN PATENT DOCUMENTS

| | | |
|---|---|---|
| DE | 102011075454 B4 | 7/2016 |
| WO | WO 2020081123 A1 | 4/2020 |

OTHER PUBLICATIONS

Duan, Yunsuo et al.; "A Continuously Adjustable 32-Ch Head Coil
Array for MRI at 3T. In: ISMRM Annual Meeting."; 2021.

* cited by examiner

HEAD-NECK COIL ARRANGEMENT FOR MAGNETIC RESONANCE APPLICATIONS

CROSS-REFERENCE TO RELATED APPLICATION(S)

The present application claims priority under 35 U.S.C. § 119 to German Patent Application No. 10 2023 212 723.7, filed Dec. 14, 2023, the entire contents of which is incorporated herein by reference.

FIELD

One or more example embodiments of the present invention provide a head-neck coil arrangement for magnetic resonance applications on a patient, wherein the coil arrangement has a base part, made of a rigid material, with which the coil arrangement can be placed on a patient couch, wherein the coil arrangement has an upper additional part in which upper local coils are arranged, wherein the upper additional part is movably arranged on the base part and/or is embodied to be intrinsically movable, so a spacing of the upper local coils from the facial area, from the neck area and from the upper chest area of the patient can be adjusted, wherein the coil arrangement has a lower additional part in which lower local coils are arranged, and wherein the lower additional part in a lower region and the upper additional part in an upper region are connected to the base part, so the base part, the lower additional part and the upper additional part can be handled manually as one unit by a user.

BACKGROUND

The Applicant points out that independent of the grammatical term usage (here, by way of example, the terms "patient" and "user"), individuals with male, female or other gender identities are included within the term.

A coil arrangement of this kind is known, for example, from WO 2020/081 123 A1.

From DE 10 2011 075 454 B4 a head-neck coil arrangement for magnetic resonance applications is known, which has a base part made of a rigid material, with which the coil arrangement can be placed on a patient couch. The coil arrangement also has an upper additional part in which upper local coils are arranged. The upper additional part is movably arranged on the base part, so a spacing of the upper local coils from the facial area, from the neck area and from the upper chest area of the patient can be adjusted. The lower additional part is connected to the base part in an upper region, so the base part and the upper additional part can be handled manually as one unit by a user.

The head-neck region is often treated in radiation therapy (often designated by RT for radiotherapy). The associated treatment planning is increasingly based on imaging magnetic resonance technology. Within the context of radiation therapy, the positioning of the patient during the planning of the treatment has to coincide exactly with the positioning of the patient during implementation of the treatment. For this reason, precise immobilization of the relevant regions of the body is necessary. Furthermore, it is necessary to acquire the three-dimensional anatomy of the patient with high resolution (sometimes 1 mm, and even more accurately) and high image contrast. In addition, the time necessary for the image acquisition should also be as short as possible. This is particularly critical in the case of stereotactic irradiation and in the case of irradiation of regions in whose immediate vicinity endangered risk structures are situated.

Head-neck coil arrangements, which are used in the context of conventional diagnosis systems, are often not compatible with systems which are used for treatment planning. In this case more complex structures tend to be used, utilizing standard coils and special holding and securing mechanisms, devices and/or means, and other immobilization aids. On the one hand, this is time-consuming and inconvenient for a user and can also result in a reduced image quality.

In many cases, imaging longitudinally beyond the neck up to the shoulders and over the entire width of the body of the patient, also on the shoulders, is required, moreover, for planning radiation therapy.

Various immobilization systems are known in the prior art, by which the head, the neck and the shoulders of the patient can be fixed. For example, there are masks made of thermoplastic material, which adhere to the skin, or frames made of stiff material, which may be placed around the head. The associated space requirement varies from case to case. As a whole it is important to adapt the arrangement of the local coils to the specific anatomy of the patient and to the specifically desired immobilization. In many cases a standard coil is put under the head (i.e. at the back of the head, posterior direction). A further standard coil is put in the anterior direction (i.e. on the face) in this case. Alternatively, two standard coils are used which are placed from the posterior direction, once on the left and once on the right, past the head of the patient to the anterior and are then fixed.

SUMMARY

At least one object of one or more example embodiments of the present invention is to create possibilities via which good immobilization and a high image quality can be achieved with straightforward handling of a head-neck coil arrangement. Furthermore, it should be possible to use the head-neck coil arrangement flexibly.

At least this object is achieved by a head-neck coil arrangement with the features described in the claims. Advantageous embodiments of the head-neck coil arrangement are the subject-matter of dependent claims and are described herein.

Inventively, a head-neck coil arrangement of the type mentioned in the introduction is embodied in that, viewed from anterior to posterior, the lower additional part can be adjusted in height relative to the base part, so a spacing of the lower local coils from the back of the head of the patient can be adjusted.

As a result, an elevation of the lower additional part, in particular, can be adjusted as required such that it can be used with an RT overlay as well as without an overlay of this kind and when an RT overlay is used, can be used above and below the RT overlay. In both cases the spacing of the lower local coils from the back of the head of the patient can be minimized as far as possible and, as a result, the image quality can be optimized. The immobilization can be implemented as required without an overlay as well as with an overlay. Farther-reaching modifications to the head-neck coil arrangement are not necessary.

It is possible that the lower additional part has a mechanical structure made of a flexible material and that the lower local coils are embedded in the mechanical structure. In this case the possibility of height adjustment results entirely due to the material of the lower additional part. Preferably, the lower local coils are embodied as flexible coils in this case.

Alternatively it is possible that the lower additional part is embodied as a mechanically rigid element and the base part has a plurality of plug positions for the lower additional part which are vertically offset, viewed from anterior to posterior. In this case the height setting can be selected as a result of the plug positions in which the lower additional part is plugged.

Preferably, the upper additional part is detachably connected to the base part. This embodiment makes it easier, in particular, for the patient to lie down or get up and also makes cleaning and sterilization of the head-neck coil arrangement easier after use.

It is possible that the upper additional part comprises a left and a right side part which can be unfolded, viewed from the base part, to the left and right. In many cases—as a rule, be it alternatively, in exceptional cases but also in addition to the presence of two side parts—it is advantageous, however, if the upper additional part is hinged on the base part in such a way that the upper additional part can be unfolded in the superior direction. This embodiment is, in particular, constructionally simple to implement and very effective.

Preferably, in this case the upper additional part, viewed from superior to inferior, has a plurality of links which are each connected to one another via a hinge, so the upper additional part is embodied in the manner of a link chain. The upper local coils are arranged in the links in this embodiment. As a result, the upper additional part can be put on the face, the neck and the upper chest area of the patient in a manner similar to a flexible chain. This applies, in particular if, viewed from superior to inferior, one of the hinges respectively is arranged in the forehead area, in the chin area and in the neck area of the patient. In addition, further hinges or flexible or deformable coil portions can be present between these hinges.

In a further preferred embodiment, the upper additional part has a mechanical structure made of a flexible material and the upper local coils are embedded in the mechanical structure. In this case the possibility of adjusting to the anatomy of the patient results entirely of its own accord. Preferably, the upper local coils are embodied as flexible coils in this case.

Preferably, the base part has guide elements which interact with corresponding guide elements of the patient couch and guide the base part, when it is placed on the patient couch, relative to the patient couch. This results in a simple robust fixing of the head-neck coil arrangement on the patient couch. Preferably, the guide elements provide guiding at an angle which is between 30° and 60°.

Preferably, electrical plug-in connectors for transmitting electrical signals between the lower and upper local coils and an evaluation device (also referred to as an evaluation facility) for magnetic resonance signals are arranged on the base part in such a way that when the base part is placed on the patient couch, they automatically make contact with corresponding mating connectors of the patient couch. As a result a separate procedure for electrically connecting the head-neck coil arrangement is omitted. Handling is thus simplified.

However, it is also possible that while electrical plug-in connectors for transmitting electrical signals between the lower and upper local coils and the evaluation device are arranged on the base part, the plug-in connectors have to be separately connected and plugged in, i.e. independently of the placement of the base part on the patient couch.

BRIEF DESCRIPTION OF THE DRAWINGS

The above-described properties, features and advantages of this invention and the manner in which they are achieved will become clearer and more understandable in conjunction with the following description of the exemplary embodiments which will be explained in more detail in connection with the drawings. In a schematic representation in the drawings.

DETAILED DESCRIPTION

Figure 1:
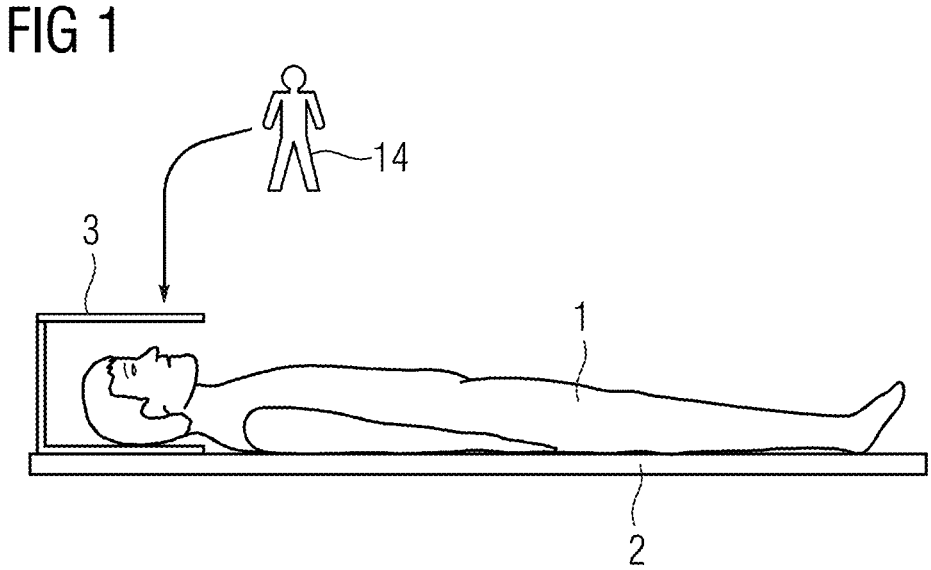
FIG. 1 shows a patient couch in a patient and a head-neck coil arrangement.

According to FIG. 1, a 3D image of a patient 1 is to be created via an imaging magnetic resonance system (not represented). The 3D image can be utilized, for example, in the context of planning radiation therapy. The patient 1 is "arranged" on a patient couch 2 in order to create the 3D image. In many cases the "arranging" consists in the patient 1 lying on the patient couch 2 and, more precisely, with his "reverse side" downwards. In many cases an overlay is arranged on the top of the patient couch 2, so the patient 1 is not "arranged" directly on the patient couch 2 but on the overlay.

Reference will be made below to various direction-like designations. The terms hereinafter have the following meanings:

"Posterior" is the "reverse side" of the patient 1, i.e. back of the head, back, buttocks and back of the legs down to the heels of the patient 1.

"Anterior" is the "front side" of the patient 1, i.e. face, chest, stomach and front of the legs down to the toes of the patient 1.

"Superior" is the "top" of the patient 1, i.e. essentially the cranium of the patient 1.

"Inferior" is the "bottom" of the patient 1, i.e. essentially the soles of the feet of the patient 1.

Based on these meanings, the wording "viewed from anterior to posterior" means the height direction or (herewith in essence synonymously) the elevation relative to the patient couch 2. Analogously, the wording "viewed from superior to inferior" means the longitudinal direction of the patient couch 2.

A head-neck coil arrangement 3 for magnetic resonance applications, hereinafter referred to as a coil arrangement 3 for short, is arranged on the patient couch 2. As a rule, the coil arrangement 3 (or parts of the coil arrangement 3, for example a posterior part, in particular the base part 4 mentioned below) is arranged before arranging the patient 1 on the patient couch 2. According to FIG. 2, the coil arrangement 3 has a base part 4, an upper additional part 5 and a lower additional part 6. The base part 4 consists of a rigid material. Within the context of embodiments of the present invention the term "rigid" can include that the corresponding rigid part (for example, the base part 4) is surrounded by a soft casing, which can yield—for example—in a range of approx. 1 mm to ca. 2 mm. In order to arrange the coil arrangement 3 on the patient couch 2, the coil arrangement 3 is placed with the base part 4 on the patient couch 2.

In order to arrange the coil arrangement 3 on the patient couch 2, the base part 4 can have guide elements 7 which interact with corresponding guide elements 8 of the patient couch 2. When placed on the patient couch 2 the base part 4 is guided relative to the patient couch 2 by the interaction of the guide elements 7, 8. In particular, the guide elements 7, 8 can be embodied and oriented in such a way that the guide elements 7, 8 guide the base part 4, when placed on the patient couch 2, relative to the patient couch 2 at an angle α which is between 30° and 60°. Corresponding embodiments are known to persons skilled in the art and are described, for example, in DE 10 2008 063 629 A1.

Local coils 9, hereinafter referred to as upper local coils 9, are arranged in the upper additional part 5. Local coils 10, hereinafter referred to as lower local coils 10, are similarly arranged in the lower additional part 6. The terms "upper local coils 9" and "lower local coils 10" are used in the generic sense. Therefore, in the individual case it is also possible for only a single upper or lower local coil 9, 10 to be present. However, as a rule, a plurality of upper and lower local coils 9, 10 are present.

Via the upper and lower local coils 9, 10 it is possible to capture magnetic resonance signals which were previously excited in the patient 1 in a known manner. The magnetic resonance signals (i.e. electrical signals) are transmitted to an evaluation device 11 (also referred to as an evaluation facility). If necessary, the magnetic resonance signals can be preamplified in advance within the coil arrangement 3. The coil arrangement 3 has electrical plug-in connectors 12 for transmitting the magnetic resonance signals. The electrical plug-in connectors 12 are preferably arranged on the base part 4. At least the magnetic resonance signals are thus transmitted between the upper and lower local coils 9, 10 and the evaluation device 11. Further electrical signals can possibly also be transmitted via the plug-in connectors 12, for example control signals from the evaluation device 11 to the upper and lower local coils 9, 10.

The plug-in connectors 12 can in principle be arranged on the base part 4 as desired. An arrangement on the base part 4 corresponding to the representation in FIG. 2 in such a way that when the base part 4 is placed on the patient couch 2 the plug-in connectors 12 automatically make contact with corresponding mating connectors 13 of the patient couch 2 is preferred. Corresponding embodiments are known to persons skilled in the art in this case too and are described, for example, in DE 10 2008 063 629 A1 which has already been mentioned.

The lower additional part 6 is connected to the base part 4 in a lower region. Owing to the site of the connection of the lower additional part 6 to the base part 4, the lower local coils 10 are in the posterior location. As a result, magnetic resonance signals, in particular, can be captured by the lower local coils 10, which signals originate from the region of the back of the head, the back of the neck and/or of the back in the region of the shoulder blades of the patient 1, i.e. from rearward areas of the patient 1.

Analogously, the upper additional part 5 is connected to the base part 4 in an upper region. Owing to the site of the connection of the upper additional part 5 to the base part 4, the upper local coils 9 are in the anterior location. As a result, magnetic resonance signals, in particular, can be captured by the upper local coils 9, which signals originate from the region of the face, the front of the neck and/or the chest in the region of the clavicles of the patient 1, i.e. from front areas of the patient 1.

Owing to the connection of the upper and of the lower additional parts 5, 6 to the base part 4, the base part 4, the lower additional part 5 and the upper additional part 6 can be handled manually as one unit by a user 14 (see FIG. 1). The coil arrangement 3 can therefore be handled manually in its entirety as a unit. The user 14 can place the coil arrangement 3 manually (using muscular strength) on the patient couch 2.

The upper additional part 5 is also movably arranged on the base part 4 and/or is intrinsically movable. As a result, a spacing of the upper local coils 9 from the facial area, from the (front) neck area and from the upper chest area of the patient 1 can be adjusted. In the case of the embodiment according to FIG. 2, for example, on the one hand the upper additional part 5 is hinged on the base part 4 in such a way that the upper additional part 5 can be unfolded in the superior direction. The associated hinge is designated by the reference numeral 15 in FIG. 2, the possible unfolding indicated by an arrow 16.

Figure 2:
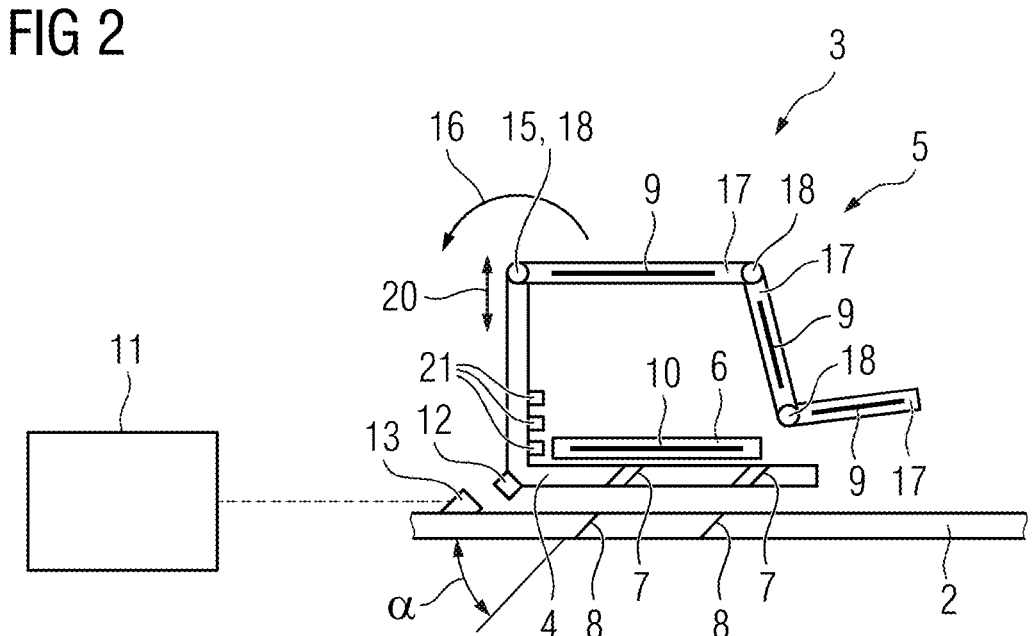
FIG. 2 shows part of FIG. 1 without the patient.

In the case of the embodiment according to FIG. 2, viewed from superior to inferior, the upper additional part 5 also has a plurality of links 17 which are each connected to one another via a hinge 18. The upper additional part 5 is thus embodied in the manner of a link chain. FIG. 2 represents the minimal configuration in which, viewed from superior to inferior, one of the hinges 18 respectively is arranged in the forehead area, in the chin area and in the neck area of the patient 1. However, in addition, further hinges 18, and therewith also additional links 17, could also be present between the hinges 18. The upper local coils 9 are arranged in the links 17 in the embodiment of FIG. 2.

Figure 3:
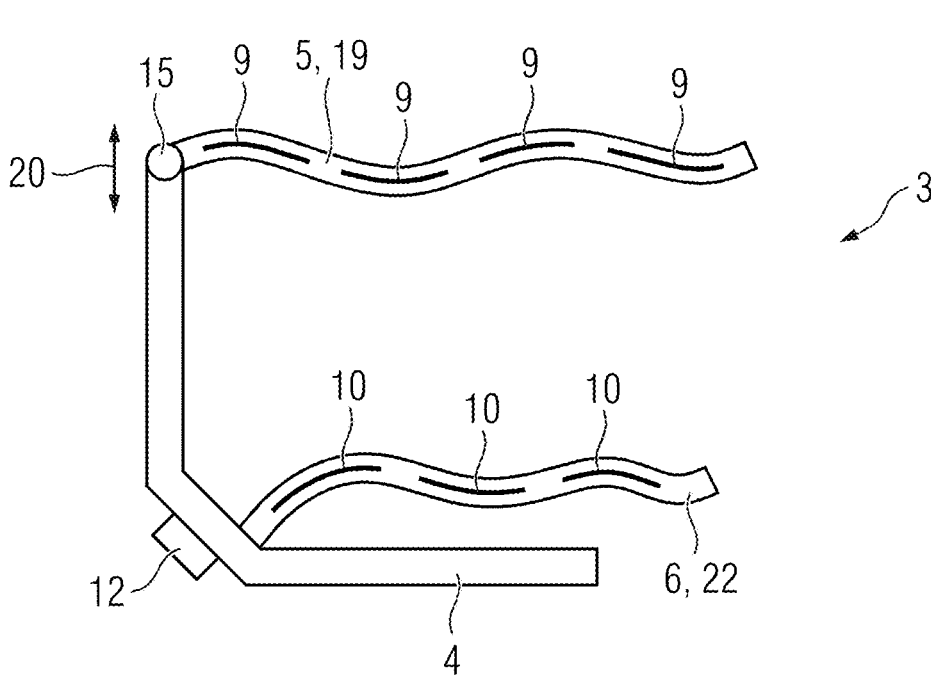
FIG. 3 shows an alternative embodiment to FIG. 2.

As an alternative to an embodiment of the upper additional part 5 as a link chain, according to FIG. 3 it is possible that the upper additional part 5 has a mechanical structure 19 made from a flexible material. In this case the upper local coils 9 are embedded in the mechanical structure 19. Preferably, the upper local coils 9 are still designed as flexible coils in this case. This is indicated in FIG. 3 by the upper local coils 9 not being drawn with a straight but a curved design. The hinge 15 can in this case still be present in accordance with the representation in FIG. 3. However, it can also be omitted-depending on the flexibility of the mechanical structure 19. The flexibility of the mechanical structure 19 can be such that it already adapts to its placement of its own accord as a result of its own weight. Alternatively, the flexibility of the mechanical structure 19 can be such that it is plastically deformed only due to an additional application of force.

It is also possible, insofar as the upper additional part 5 is concerned, to implement a mixed form between the embodiments of FIGS. 2 and 3. In this case, on the one hand the links 17 and the hinges 18 are present between the links 17, but the links 17 are not completely rigid, rather they are still flexible to a certain extent.

Figure 4:
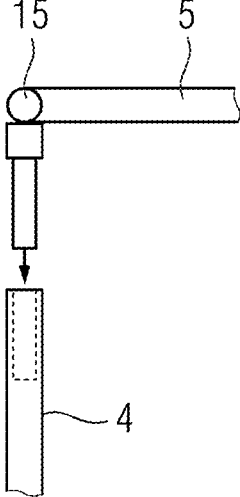
FIG. 4 shows portions of a base part and an upper additional part.

As indicated by an arrow 20 in FIGS. 2 and 3, it is also possible that the hinge 15 located furthest away in the superior direction can be adjusted in height relative to the base part 4. As a result it is possible to achieve, in particular, that the link 17 of the link chain adjoining the hinge 15 can be optimally brought up to the face of the patient 1. Furthermore, in accordance with the representation in FIG. 4 it can be possible that the upper additional part 5 is detachably connected to the base part 4.

Viewed from anterior to posterior, the lower additional part 6 can be adjusted in height relative to the base part 4. As a result, a spacing of the lower local coils 10 from the back of the head of the patient 1 can be adjusted. For example, in accordance with the representation in FIG. 2, the base part 4 can have a plurality of plug positions 21 for the lower additional part 6. Viewed from anterior to posterior, the plug positions 21 are vertically offset in this case. The lower additional part 6 can be embodied as a mechanically rigid element in this case. The elevation of the lower additional part 6 is defined by the plug position 21 in which the lower additional part 6 is plugged.

As an alternative to a rigid embodiment of the lower additional part 6, in accordance with FIG. 3 it is possible that the lower additional part 6 has a mechanical structure 22 made from a flexible material. In this case the lower local coils 10 are embedded in the mechanical structure 22. Preferably, the lower local coils 10 are still embodied as flexible coils in this case. This is indicated in FIG. 3 in that the lower local coils 10 are not drawn with a straight but a curved design. Just like the mechanical structure 19, the flexibility of the mechanical structure 22 can be such that it already adapts to its placement of its own accord as a result of its own weight or it is plastically deformed only due to an additional application of force.

The embodiment of the upper additional part 5 and the embodiment of the lower additional part 6 are mutually independent. It is therefore possible to implement the specific combinations not only in accordance with the representations in FIGS. 2 and 3, but it is also possible, for example, to embody the upper additional part 5 in accordance with the representation in FIG. 3 and the lower additional part 6 in accordance with the representation in FIG. 2. Conversely, it is also possible to embody the upper additional part 5 in accordance with the representation in FIG. 2 and the lower additional part 6 in accordance with the representation in FIG. 3.

In summary, embodiments of the present invention thus relate to the following facts:

A head-neck coil arrangement 3 for magnetic resonance applications on a patient 1 has a base part 4, made from a rigid material, with which the coil arrangement 3 can be placed on a patient couch 2. The coil arrangement 3 also has an upper additional part 5 in which upper local coils 9 are arranged. The upper additional part 5 is movably arranged on the base part 4 and/or is embodied to be intrinsically movable, so a spacing of the upper local coils 9 from the facial area, from the neck area and from the upper chest area of the patient 1 can be adjusted. The coil arrangement 3 also has a lower additional part 6 in which lower local coils 10 are arranged. The lower additional part 6 is connected to the base part 4 in a lower region, the upper additional part 5 in an upper region. As a result, the base body 4, the lower additional part 6 and the upper additional part 5 can be handled manually as one unit by a user 14. Viewed from anterior to posterior, the lower additional part 6 can be adjusted in height relative to the base part 4, so a spacing of the lower local coils 10 from the back of the head of the patient 1 can be adjusted.

One or more embodiments of the present invention have many advantages. The coil arrangement 3 can thus be used universally and can be adapted as required to the anatomy of the patient 1 and to other needs. For example, immobilization aids can be introduced as required into the region between the upper additional part 5 and the patient couch 2. The immobilization aids can be arranged above or below the lower additional part 6 as required, for example with an arrangement of the lower additional part 6 in the top plug position 21, below the lower additional part 6 and with an arrangement of the lower additional part 6 in the bottom plug position 21, above the lower additional part 6. This can be possible even with an embodiment of the lower additional part 6 with a mechanical structure 22 made from a flexible material. In particular, these two positionings can be expedient with an RT overlay.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

Although the present invention has been illustrated and described in detail by example embodiments, it is not limited by the disclosed examples and a person skilled in the art can derive other variations herefrom without departing from the scope of the present invention

What is claimed is:

1. A head-neck coil arrangement for magnetic resonance applications on a patient, the head-neck coil arrangement comprising:

a base part composed of a rigid material, the base part configured to be placed on a patient couch;

an upper additional part in which upper local coils are arranged, wherein the upper additional part is at least one of movably arranged on the base part or configured to be intrinsically movable, such that a spacing of the upper local coils from a facial area, a neck area and an upper chest area of the patient is adjustable; and a lower additional part in which lower local coils are arranged, wherein the lower additional part in a lower region and the upper additional part in an upper region are connected to the base part, the base part, the lower additional part and the upper additional part are configured to be handled manually as one unit by a user, the lower additional part, viewed from anterior to posterior, is configured to be adjusted in height relative to the base part such that a spacing of the lower local coils from a back of a head of the patient are adjustable, the lower additional part is a mechanically rigid element, and the base part has a plurality of plug positions for the lower additional part which are vertically offset, viewed from the anterior to the posterior.

2. The head-neck coil arrangement as claimed in claim 1, wherein the lower additional part has a mechanical structure composed of a flexible material, and wherein the lower local coils are embedded in the mechanical structure.

3. The head-neck coil arrangement as claimed in claim 2, wherein the lower local coils are flexible coils.

4. The head-neck coil arrangement as claimed in claim 1, wherein the upper additional part is detachably connected to the base part.

5. The head-neck coil arrangement as claimed in claim 1, wherein the upper additional part is hinged to the base part such that the upper additional part is configured to unfold in a superior direction.

6. The head-neck coil arrangement as claimed in claim 5, wherein the upper additional part, viewed from superior to inferior, has a plurality of links, which are each connected to one another via a hinge, such the upper additional part is embodied as a link chain, and wherein the upper local coils are arranged in the plurality of links.

7. The head-neck coil arrangement as claimed in claim 6, wherein, when viewed from superior to inferior, a respective hinge is arranged in a forehead area, in a chin area and in the neck area of the patient.

8. The head-neck coil arrangement as claimed in claim 1, wherein the upper additional part has a mechanical structure composed of a flexible material, and wherein the upper local coils are embedded in the mechanical structure.

9. The head-neck coil arrangement as claimed in claim 8, wherein the upper local coils are flexible coils.

10. The head-neck coil arrangement as claimed in claim 1, wherein the base part has guide elements configured to interact with corresponding guide elements of the patient couch and guide the base part relative to the patient couch when the base part is placed on the patient couch.

11. The head-neck coil arrangement as claimed in claim 10, wherein the guide elements guide the base part relative to the patient couch at an angle between 30° and 60°.

12. The head-neck coil arrangement as claimed in claim 10, further comprising:

electrical plug-in connectors arranged on the base part, the electrical plug-in connectors configured to transmit electrical signals between the lower local coils and the upper local coils and an evaluation device for magnetic resonance signals, the electrical plug-in connectors being arranged such that when the base part is placed on the patient couch, the electrical plug-in connectors contact corresponding mating connectors of the patient couch.

13. The head-neck coil arrangement as claimed in claim 1, further comprising:

electrical plug-in connectors arranged on the base part, the electrical plug-in connectors being configured to transmit electrical signals between the lower local coils and the upper local coils and an evaluation device for magnetic resonance signals.

14. The head-neck coil arrangement as claimed in claim 4, wherein the upper additional part is hinged to the base part such that the upper additional part is configured to unfold in a superior direction.

15. The head-neck coil arrangement as claimed in claim 5, wherein the upper additional part has a mechanical structure composed of a flexible material, and wherein the upper local coils are embedded in the mechanical structure.

16. The head-neck coil arrangement as claimed in claim 4, wherein the base part has guide elements configured to interact with corresponding guide elements of the patient couch and guide the base part relative to the patient couch when the base part is placed on the patient couch.

17. The head-neck coil arrangement as claimed in claim 11, further comprising:

electrical plug-in connectors arranged on the base part, the electrical plug-in connectors configured to transmit electrical signals between the lower local coils and the upper local coils and an evaluation device for magnetic resonance signals, the electrical plug-in connectors being arranged such that when the base part is placed on the patient couch, the electrical plug-in connectors contact corresponding mating connectors of the patient couch.

18. The head-neck coil arrangement as claimed in claim 4, further comprising:

electrical plug-in connectors arranged on the base part, the electrical plug-in connectors being configured to transmit electrical signals between the lower local coils and the upper local coils and an evaluation device for magnetic resonance signals.

19. The head-neck coil arrangement as claimed in claim 11, further comprising:

electrical plug-in connectors arranged on the base part, the electrical plug-in connectors being configured to transmit electrical signals between the lower local coils and the upper local coils and an evaluation device for magnetic resonance signals.

* * * * *